US009956407B2

(12) United States Patent
Hubert-Brierre (10) Patent No.: US 9,956,407 B2
(45) Date of Patent: May 1, 2018

(54) TONAL DEAFNESS COMPENSATION IN AN AUDITORY PROSTHESIS SYSTEM

(71) Applicant: Cochlear Limited, Macquarie University, NSW (AU)

(72) Inventor: Florent Maxime Hubert-Brierre, Meise (BE)

(73) Assignee: Cochlear Limited, Macquarie University, NSW (AU)

( * ) Notice: Subject to any disclaimer, the term of this patent is extended or adjusted under 35 U.S.C. 154(b) by 282 days.

(21) Appl. No.: 14/816,323

(22) Filed: Aug. 3, 2015

(65) Prior Publication Data

US 2016/0030744 A1  Feb. 4, 2016

Related U.S. Application Data

(60) Provisional application No. 62/032,776, filed on Aug. 4, 2014.

(51) Int. Cl.
*A61N 1/36* (2006.01)
*A61N 1/372* (2006.01)
(Continued)

(52) U.S. Cl.
CPC ..... *A61N 1/36032* (2013.01); *A61N 1/36036* (2017.08); *A61N 1/37247* (2013.01);
(Continued)

(58) Field of Classification Search
CPC ........ A61F 11/04; A61N 1/36; A61N 1/36032
(Continued)

(56) References Cited

U.S. PATENT DOCUMENTS 4,577,641 A  3/1986 Hochmair et al.
5,995,924 A  11/1999 Terry
(Continued)

FOREIGN PATENT DOCUMENTS

WO  98/54696 A1  12/1998

OTHER PUBLICATIONS

International Search Report and Written Opinion in counterpart International Application No. PCT/IB2015/055916, dated Dec. 17, 2015, 9 pages.
(Continued)

*Primary Examiner* — Carl H Layno
*Assistant Examiner* — Jon Eric C Morales
(74) *Attorney, Agent, or Firm* — Edell, Shapiro & Finnan, LLC (57) ABSTRACT

Embodiments presented herein are generally directed to techniques for compensating for tonal deafness experienced by a recipient of an auditory prosthesis. More specifically, an auditory prosthesis system includes an external device configured to generate a graphical representation that enables the recipient to compensate for reduced tonal perception associated with delivery of the stimulation signals representative of speech signals. The external device is configured to analyze received speech signals to determine vocal articulator movement of the speaker of the speech signals and/or emotion of the speaker. The external device is further configured to display one or more animated visual cues representative of the detected vocal articulator movement and/or emotion.

20 Claims, 8 Drawing Sheets

(51) Int. Cl.
*G10L 21/10* (2013.01)
*A61N 1/05* (2006.01)
*H04R 25/00* (2006.01)

(52) U.S. Cl.
CPC ............ *G10L 21/10* (2013.01); *A61N 1/0541* (2013.01); *G10L 2021/105* (2013.01); *H04R 25/554* (2013.01); *H04R 2225/55* (2013.01); *H04R 2225/67* (2013.01)

(58) Field of Classification Search
USPC .......................................................... 607/57
See application file for complete search history.

(56) References Cited

U.S. PATENT DOCUMENTS

| | | | |
|---|---|---|---|
| 6,377,925 B1* | 4/2002 | Greene, Jr. | G10L 21/06 379/52 |
| 7,222,075 B2 | 5/2007 | Petrushin | |
| 2008/0049946 A1 | 2/2008 | Heller et al. | |
| 2009/0076569 A1* | 3/2009 | Busby | A61N 1/36032 607/57 |
| 2013/0251179 A1 | 9/2013 | Aschoff et al. | |
| 2014/0050341 A1 | 2/2014 | Flynn et al. | |

OTHER PUBLICATIONS

Morishima, et al., "An Intelligent Facial Image Coding Driven by Speech and Phoneme," 1989 International Conference on Acoustics, Speech, and Signal Processing (ICASSP-89), May 1989, pp. 1795-1798.

Nakamura, et al., "Speech-To-Lip Movement Synthesis Maximizing Audio-Visual Joint Probability Based on EM Algorithm," 1998 IEEE Second Workshop on Multimedia Signal Processing, Dec. 1998, pp. 53-58.

Yamamoto, et al., "Lip movement synthesis from speech based on Hidden Markov Models," Speech Communication, vol. 26, Issues 1-2, Oct. 1998, pp. 105-115.

Nakamura, "Lip Motion Generation from Audio Signals based on Hidden Markov Models," The 5th ATR Symposium on Face and Object Recognition, Jul. 1999, pp. 47-49.

Polzin, et al., "Detecting emotions in speech," Proceedings of the CMC, vol. 16, Jan. 1998, 7 pages.

Edge, et al., "Model-based Synthesis of Visual Speech Movements from 3D Video," ACM Transactions on Graphics, vol. 2, No. 3, Sep. 2001, pp. 1-7.

* cited by examiner

TONAL DEAFNESS COMPENSATION IN AN AUDITORY PROSTHESIS SYSTEM

CROSS-REFERENCE TO RELATED APPLICATIONS

This application claims priority to U.S. Provisional Application No. 62/032,776 entitled "Tonal Deafness in an Auditory Prosthesis System," filed Aug. 4, 2014, the content of which is hereby incorporated by reference herein.

BACKGROUND

Field of the Invention

The present invention relates generally to auditory prostheses system.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable electrically-stimulating auditory prostheses that stimulate nerve cells of the recipient's auditory system in other ways (e.g., electrical, optical and the like). A cochlear implant is one type of electrically-stimulating auditory prosthesis that may be proposed when the sensorineural hearing loss is due to the absence or destruction of the cochlea hair cells that transduce acoustic signals into nerve impulses. An auditory brainstem stimulator is another type of electrically-stimulating auditory prosthesis that might also be proposed when a recipient experiences sensorineural hearing loss due to damage to the auditory nerve.

SUMMARY

In one aspect of the invention, an auditory prosthesis system is provided. The auditory prosthesis system comprises a cochlear implant having a plurality of stimulating contacts configured to deliver stimulation signals to a recipient and an external device. The external device comprises an interface configured to communicate with the cochlear implant, a display screen, and at least one processor. The at least one processor is configured to provide received speech signals to the cochlear implant for use in delivering stimulation signals representative of the received speech signals to the recipient, and display, at the display screen, a graphical representation configured to enable the recipient to compensate for reduced tonal perception associated with delivery to the recipient of the stimulation signals representative of the received speech signals.

In another aspect of the invention, a method performed at a system that includes an implantable auditory prosthesis and an external device is provided. The method comprises receiving speech signals forming part of a voice call, analyzing, at the external device, the received speech signals, sending the speech signals to the implantable auditory prosthesis for use in generating stimulation signals representative of the received speech signals, wherein delivery of the stimulation signals to the recipient results in reduced tonal perception of the received speech signals, and displaying, at the external device a graphical representation that enables the recipient of the implantable auditory prosthesis to compensate for the reduced tonal perception associated with delivery of stimulation signals representative of the speech signals.

In another aspect of the invention, a method is provided. The method comprises: determining a degree of tonal deafness of a recipient of an implantable auditory prosthesis, wherein the implantable auditory prosthesis is configured to operate with an external device configured to display a graphical representation that enables the recipient to compensate for tonal deafness associated with delivery of stimulation signals to the recipient, and setting a predetermined display mode for the graphical representation based on the degree of the tonal deafness of the recipient.

BRIEF DESCRIPTION OF THE DRAWINGS

Embodiments of the present invention are described herein in conjunction with the accompanying drawings, in which.

DETAILED DESCRIPTION

Embodiments presented herein are generally directed to techniques for compensating for tonal deafness experienced by a recipient of an auditory prosthesis. More specifically, an auditory prosthesis system includes an external device configured to generate a graphical representation that enables the recipient to compensate for reduced tonal perception associated with delivery of the stimulation signals representative of speech signals. The external device is configured to analyze received speech signals to determine vocal articulator movement of the speaker of the speech signals and/or emotion of the speaker. The external device is further configured to display one or more animated visual cues representative of the detected vocal articulator movement and/or emotion.

There are different types of auditory prostheses that may be partially or fully implanted into a recipient, including middle ear auditory prostheses, direct acoustic stimulators, and electrically simulating auditory prostheses such as auditory brain stimulators and cochlear implants. It is to be appreciated that the tonal deafness compensation techniques in accordance with embodiments presented herein may be used in connection with any of the above or other auditory prostheses. However, merely for ease of description, embodiments of the tonal deafness compensation techniques are primarily described herein with reference to an illustrative auditory prosthesis, namely a cochlear implant.

Figure 1:
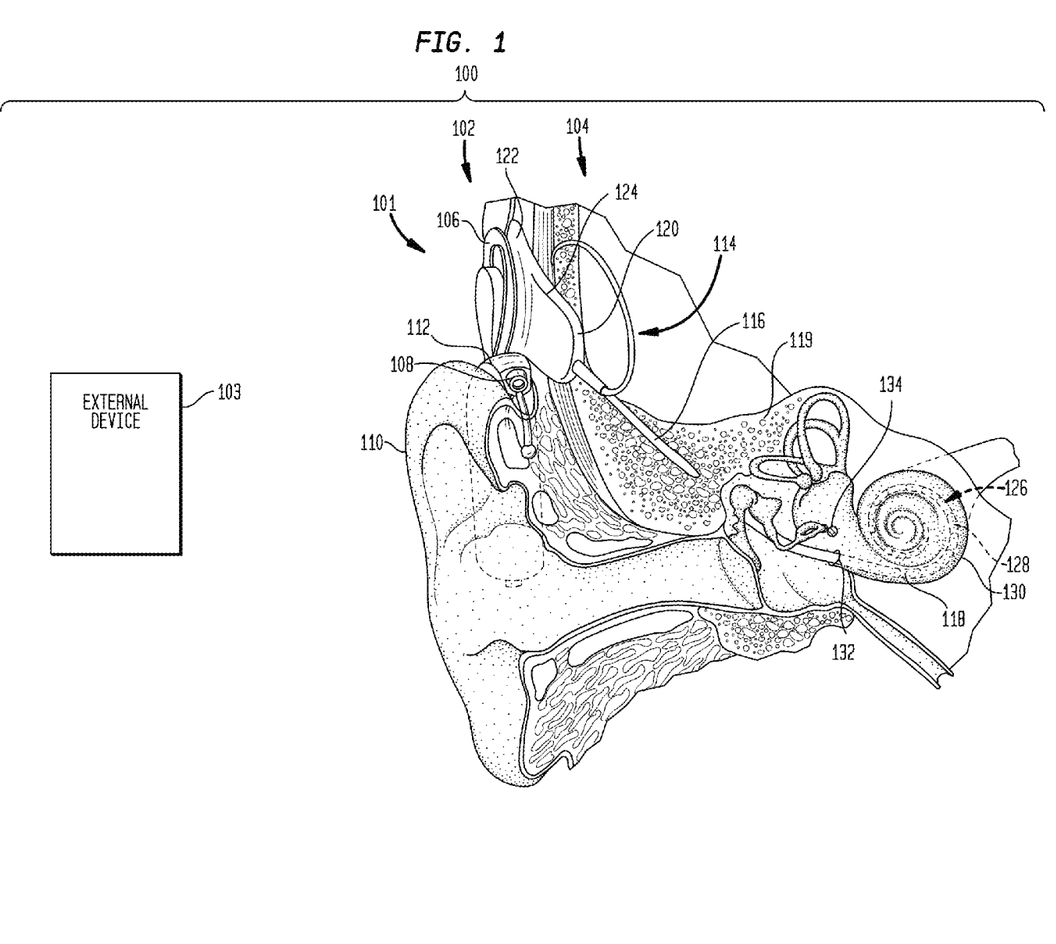
FIG. 1 is a schematic diagram of an implantable auditory prosthesis system in accordance with embodiments of the present invention.

FIG. 1 is perspective view of an exemplary auditory prosthesis system 100 in which tonal deafness compensation techniques in accordance with embodiments presented herein may be implemented. The auditory prosthesis system 100 comprises a cochlear implant 102 and an external device 103. As described further below, the external device 103 is an electronic component configured to communicate with the cochlear implant 102.

The cochlear implant 102 includes an external component 101 and an internal or implantable component 104. The external component 101 is directly or indirectly attached to the body of the recipient and typically comprises an external coil 106 and, generally, a magnet (not shown in FIG. 1) fixed relative to the external coil 106, one or more sound input elements 108 (e.g., microphones, telecoils, etc.) for detecting sound and a sound processing unit 112. The sound processing unit 112 may include, for example, a power source (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via a cable (not shown in FIG. 1).

FIG. 1 illustrates an example in which cochlear implant 102 includes an external component 101 with an external sound processor. It is to be appreciated that the use of an external component is merely illustrative and that the techniques presented herein may be used in arrangements having an implanted sound processor (e.g., totally implantable cochlear implants). It is also to be appreciated that the individual components referenced herein, e.g., sound input element 108 and the sound processor in sound processing unit 112, may be distributed across more than one tissue-stimulating prosthesis, e.g., two cochlear implants 102, and indeed across more than one type of device, e.g., cochlear implant 102 and a consumer electronic device or a remote control of the cochlear implant 102.

The implantable component 104 comprises an implant body 114, a lead region 116, and an elongate intra-cochlear stimulating assembly 118. The implant body 114 comprises a stimulator unit 120, an internal coil 122, and an internal receiver/transceiver unit 124, sometimes referred to herein as transceiver unit 124. The transceiver unit 124 is connected to the internal coil 122 and, generally, a magnet (not shown) fixed relative to the internal coil 122.

The magnets in the external component 101 and implantable component 104 facilitate the operational alignment of the external coil 106 with the internal coil 122. The operational alignment of the coils enables the internal coil 122 to transmit/receive power and data to/from the external coil 106. More specifically, in certain examples, external coil 106 transmits electrical signals (e.g., power and stimulation data) to internal coil 122 via a radio frequency (RF) link. Internal coil 122 is typically a wire antenna coil comprised of multiple turns of electrically insulated single-strand or multi-strand platinum or gold wire. The electrical insulation of internal coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is configured to be at least partially implanted in cochlea 130 and includes a plurality of intra-cochlear stimulating contacts 128. The stimulating contacts 128 collectively form a contact array 126 and may comprise electrical contacts and/or optical contacts.

Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120. An intra-cochlear stimulating assembly, such as stimulating assembly 118, may be a perimodiolar stimulating assembly or a non-perimodiolar stimulating assembly (e.g., lateral stimulating assembly or a mid-scala stimulating assembly).

With normal hearing, the cochlea 130 comprises three parallel fluid-filled canals or ducts, comprising the tympanic canal (scala tympani), the vestibular canal (the scala vestibuli), and the median canal (scala media), that surround the organ of Corti. Sound entering auricle 110 causes pressure changes in cochlea 130 to travel through the fluid-filled tympanic and vestibular canals. The organ of Corti, which is situated on the basilar membrane in the scala media, includes thousands of hair cells. Pressure variations in the fluid-filled tympanic and vestibular canals cause these hair cells to move, thereby causing the creation of a voltage pulse or action potential which travels along nerve fibers to the auditory areas of the brain for processing.

Generally, the place along the basilar membrane where maximum excitation of the hair cells occurs determines the perception of pitch and loudness according to the place theory. Due to this anatomical arrangement, cochlea 130 has characteristically been referred to as being "tonotopically mapped." That is, regions of cochlea 130 toward the basal region of the cochlea are responsive to high frequency signals, while regions of cochlea 130 toward the apical end are responsive to low frequency signals. These tonotopical properties of cochlea 130 are exploited in a cochlear implant by delivering stimulation signals within a predetermined frequency range to a region of the cochlea that is most sensitive to that particular frequency range.

However, current cochlear implants only include a limited number of contacts (e.g., twenty-two (22)) that are implanted in the cochlea 130. Accordingly, the location at which stimulation may be delivered to the cochlea is also limited. The limited stimulation locations available with current cochlear implants may not be restricted to the actual locations of the stimulating contacts. Rather, different stimulation strategies have been developed to stimulate other locations in the cochlea (e.g., between contacts). However, regardless of the use of different stimulation strategies, current cochlear implants lack the ability to precisely replicate the operation of the thousands of hair cells utilized in normal hearing. This inability to precisely replicate the operation of the thousands of hair cells causes some cochlear implant recipients to experience "tonal deafness." Tonal deafness refers to the lack of relative pitch perception, i.e., the inability of the recipient to distinguish/perceive different frequencies, pitch cues, or other parts of speech/sound. Tonal deafness may reduce a recipient's speech understanding and may make it difficult to perceive emotional and intonation cues carried by a speaker's voice. As such, cochlear implant recipients who suffer from tonal deafness rely heavily on facial expressions, lip movements, and body language when communicating face-to-face. These visual cues allow the cochlear implant recipient to mentally fill-in the gaps in the auditory information caused by the tonal deafness.

The lack of speech understanding, coupled within the difficulty in perceiving emotional and intonation cues significantly handicaps cochlear implant recipients when the recipient cannot see the speaker so as to obtain visual cues. Such a situation may occur, for example, when the recipient conducts a strictly/solely voice call (i.e., a traditional telephone call that is not accompanied by video), or alternatively when the speaker may not be visible (e.g., in a large room. As such, presented herein are techniques that enable a cochlear implant or other auditory prosthesis recipient to compensate for tonal deafness when the recipient is unable to obtain visual cues directly from a speaker. As described further below, the tonal deafness compensation techniques provide the cochlear implant recipient with "animated" visual cues determined based on analysis of the speaker's voice. These animated visual cues may include representative facial expressions, lip movements, and body language. In this way, the cochlear implant recipient is able to use the animated visual cues to mentally fill-in the gaps in the auditory information received through the cochlear implant.

As used herein, a voice call refers to a traditional telephone call that is not accompanied by video. As such, in accordance with the present disclosure, a voice call is different from a video call, videoconference call, telepresence call, etc. as these "calls" each include a video component.

The auditory prosthesis system 100 in accordance with embodiments presented herein includes an external device 103 that may be configured to provide the recipient with animated visual cues. An external device 103 in accordance with embodiments presented herein may be a mobile computing device, such as a mobile phone, tablet computer, laptop computer, remote control device, etc. In other embodiments, the external device 103 could be another type of computing device that has the ability to display information to a user. Other computing devices that may be used in embodiments of the present invention include, for example, Global Positioning System (GPS) units (e.g., standalone unit, a unit positioned in or attached to a vehicle/vessel, etc.), satellite phones, desktop computers, televisions attached to set-top-boxes or other equipment, etc. For ease of illustration, embodiments will be primarily described herein with reference to external device 103 as a mobile phone. In general, a mobile phone 103 has the ability to communicate with the cochlear implant 101 so as to provide the cochlear implant with audio information (i.e., provide the cochlear implant 101 with audio information associated with a voice call). As described further below, the techniques presented herein also enable the mobile phone 103 with the ability to generate and display animated visual cues based on the audio information associated with the voice call.

Figure 2:
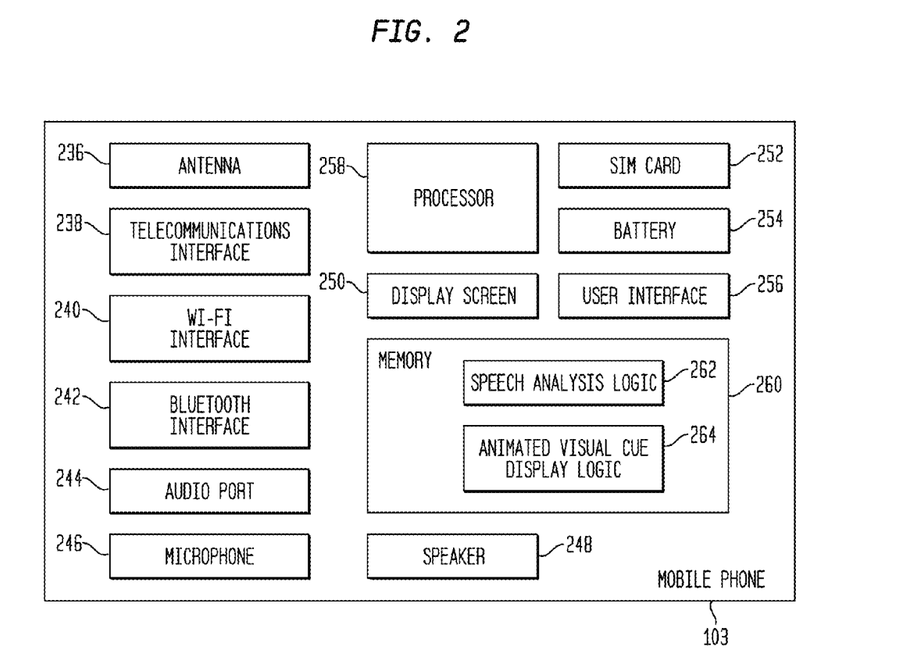
FIG. 2 is a block diagram of an external device that may form part of an implantable auditory prosthesis system in accordance with embodiments of the present invention.

FIG. 2 is a block diagram of an illustrative arrangement for mobile phone 103 in accordance with embodiments presented herein. It is to be appreciated that FIG. 2 is merely illustrative and that mobile phone 103 is not limited to the example arrangement shown in FIG. 2.

Mobile phone 103 first comprises an antenna 236 and a telecommunications interface 238 that are configured for communication on a wireless communication network for telephony services. The wireless communication network over which the radio antenna 236 and the radio interface 238 communicate may be, for example, a Global System for Mobile Communications (GSM) network, code division multiple access (CDMA) network, time division multiple access (TDMA), or other kinds of networks.

As shown in FIG. 2, mobile phone 103 also includes wireless local area network interface 240 and an infrared (IR) or Bluetooth interface 242. The wireless local area network interface 240 allows an electronic device to exchange data or connect to the Internet using, for example, 2.4 Gigahertz (GHz) Ultra high frequency (UHF) and/or 5 GHz Super high frequency (SHF) radio waves. The Bluetooth interface 242 enables the mobile phone 103 to wirelessly communicate (i.e., directly receive and transmit data to/from another device via a wireless connection). In certain examples, the Bluetooth interface 242 may be used to wireless connect the mobile phone 103 to the cochlear implant 101. It is to be appreciated that the use of a wireless local area network interface in combination with a Bluetooth interface is merely illustrative and that any other interfaces now known or later developed including, but not limited to, Institute of Electrical and Electronics Engineers (IEEE) 802.11, IEEE 802.16 (WiMAX), fixed line, Long Term Evolution (LTE), etc., may also or alternatively form part of the mobile phone 103.

Mobile phone 103 also comprises an audio port 244, one or more sound input elements, such as a microphone 246, a speaker 248, a display screen 250, a subscriber identity module or subscriber identification module (SIM) card 252, a battery 254, a user interface 256, a processor 258, and a memory 260. Memory 260 comprises speech analysis logic 262 and animated visual cue display logic 264. As described further below, speech analysis logic 262 and animated visual cue display logic 264 may be configured to execute the tonal deafness compensation techniques presented herein.

When conducting a voice call, speech signals received through antenna 236 and telecommunications interface 238 are analog to digital (A/D) converted by an A/D converter (not shown in FIG. 2), fed to audio part (also not shown in FIG. 2) that may be, for example, a codec configured to process signals under the control of processor 258. In certain embodiments, the signals are encoded so as to produce analog signals that are provided to speaker 248. The signals transmitted by speaker 248 may be detected by a microphone of the cochlear implant 101 for processing as described above for delivery of stimulation signals to the recipient (i.e., deliver stimulation signals representative of the speech signals received at the mobile phone 103). In alternative embodiments, the speech signals received by antenna 236 and telecommunications interface 238 are processed by mobile phone 103 and provided to the cochlear implant 103 through a wireless connection (e.g., via the Bluetooth interface 242) or through a wired connection (e.g., via a connection between audio port 244 and a port of the cochlear implant 101). In still other embodiments, the mobile phone 103 is a telecoil-compatible phone so as to generate a magnetic signal representative of the speech signals which can be detected by a telecoil of the cochlear implant 101.

During a voice call, speech of the cochlear implant recipient may be detected at the microphone 246 of the mobile phone. After amplification and A/D conversion, the speech signals detected by the microphone 246 may be encoded and transmitted through telecommunications interface 238 and antenna 236.

The display screen 250 is an output device, such as a liquid crystal display (LCD), for presentation of visual information to the cochlear implant recipient. The user interface 256 may take many different forms and may include, for example, a keypad, keyboard, mouse, touchscreen, display screen, etc. In one specific example, the display screen 250 and user interface 256 are combined to form a touch screen. More specifically, touch sensors or touch panels have become a popular type of user interface and are used in many types of devices. Touch panels recognize a touch input of a user and obtain the location of the touch to effect a selected operation. A touch panel may be positioned in front of a display screen, or may be integrated with a display screen. Such configurations, allow the user to intuitively connect a pressure point of the touch panel with a corresponding point on the display screen, thereby creating an active connection with the screen.

Memory 260 may comprise any one or more of read only memory (ROM), random access memory (RAM), magnetic disk storage media devices, optical storage media devices, flash memory devices, electrical, optical, or other physical/tangible memory storage devices. The processor 258 is, for example, a microprocessor or microcontroller that executes instructions for the logic stored in memory 260. Thus, in general, the memory 260 may comprise one or more tangible computer readable storage media (e.g., a memory device) encoded with software comprising computer executable instructions and when the software is executed (by the processor 258) it is operable to perform the operations described herein in connection with the tonal deafness compensation techniques. More specifically, speech analysis logic 262 and animated visual cue display logic 264 comprise software modules that, when executed by processor 258, provide the functionality described above with the tonal deafness compensation techniques.

FIG. 2 illustrates a software implementation of the tonal deafness compensation techniques (i.e., speech analysis logic 262 and animated visual cue display logic 264). That is, the mobile phone 103 executes an application that performs the tonal deafness compensation techniques. The application may be preloaded on the mobile phone 103, downloaded, etc. It is to be appreciated that this software implementation of FIG. 2 is merely illustrative, and that other implementations are possible. For example, in an alternative arrangement, speech analysis logic 262 and animated visual cue display logic 264 may be implemented fully or partially as hardware elements, such as digital logic gates in one or more application-specific integrated circuits (ASICs).

The tonal deafness compensation techniques generally comprise several phases, namely analysis of received speech signals (speech signal analysis) to correlate the speech signals with animated visual cues and display of the animated cues to the recipient. These phases are described in further detail below.

As noted a speech signal is received at mobile phone 103. During the analysis of the speech signals, the mobile phone 103 is configured to perform speech-to-lip movement synthesis. In general, speech to lip movement synthesis in accordance with embodiments presented herein refers to the translation of a sequence of detected voice features (e.g., phonemes, coarticulations, phoneme duration, pitch frequency, etc.) into movements of the visible vocal articulators, including the lips, jaw, tongue, etc. Simple synthesis techniques may utilize visemes and subsequent interpolation to correlate the speech to vocal articulator movement. In such examples, visemes may be considered to be instantaneous static targets, whereas phonemes refer to a sequence of audio or vocal tract parameters. Other types of visual synthesis techniques take map the audio data into the space of visual speech movements. These audio-visual inversion (mapping) models may be based upon, for example, Vector Quantization, Hidden Markov Models (HMMs), Artificial neural networks, Gaussian mixtures, other lookup models, etc. For example, a HMM-based system may be created to map audio parameters to marker data which can be used to animate facial features. In certain such examples, the HMM may be initially trained to recognize the training audio data, and for animation the output for each state is replaced by the distribution of visual parameters. Thus, a path through the hidden states of the HMM implies a trajectory through the articulatory space of a speaker.

In general, the speech to lip movement synthesis enables the mobile phone 103 to determine vocal data via acoustic analysis from the input audio (speech signal received at the mobile phone 103) and identify face shapes synthesized by the combination of face state and face sequence HMMs. As such, the speech to lip movement synthesis includes extraction of speech components from the received speech signals and correlation of those speech components to vocal articulator movement through, for example, application of an HMM or other synthesis technique.

It is to be appreciated that the speech to lip movement synthesis executed at mobile phone 103 may be performed in a number of different manners. Embodiments of the present invention may use any speech to lip movement synthesis technique now known or later developed.

Another part of the speech signal analysis, in addition to the speech to lip movement synthesis, is the use of voice signal analysis to detect emotion, including intonation, of the speaker. More specifically, there are a variety of temporal and spectral features that can be extracted from human speech. In certain embodiments presented herein, statistics relating to the pitch, Mel-frequency cepstral coefficients (MFCCs) and formants of speech are used as inputs to one or more algorithms that "classify" the speaker's emotion. In other embodiments, the mobile phone 103 may be configured to utilize a pre-generated database to determine the emotion associated with the speech signals. For example, the database may include statistics regarding human associations of voice parameters with emotions. When a speech signal is received, one or more features are extracted from the speech signal and the extracted features are compared to the voice parameters in the database. An emotion is selected from the database based on the comparison of the extracted voice feature to the voice parameters and is then output. The emotion of the mobile phone 103 also includes analysis of intonation such that the statements may be classified as different types (e.g., acknowledgment or query).

It is to be appreciated that the emotion and intonation synthesis executed at mobile phone 103 may be performed in a number of different manners. Embodiments of the present invention may use any emotion or intonation synthesis technique now known or later developed.

As detailed above, the mobile phone 103 analyzes the received speech signal to correlate the speech to vocal articulators (e.g., lips, tongue, jaw, etc.) and to detect emotion (including intonation). Using this information, the mobile phone 103 is configured to display, at the display screen 250, a graphical representation that enables the recipient to compensate for the tonal deafness associated with the cochlear implant 101 (i.e., compensate for the reduced tonal perception associated with delivery of stimulation signals representative of the received speech signals to the recipient's inner ear). In other words, the mobile phone 103 is configured to utilize the results of the analysis, including the speech to vocal articulator, emotion, and intonation information to generate animated visual cues that may be utilized by the recipient to compensate for his/her tonal deafness.

Figure 3A:
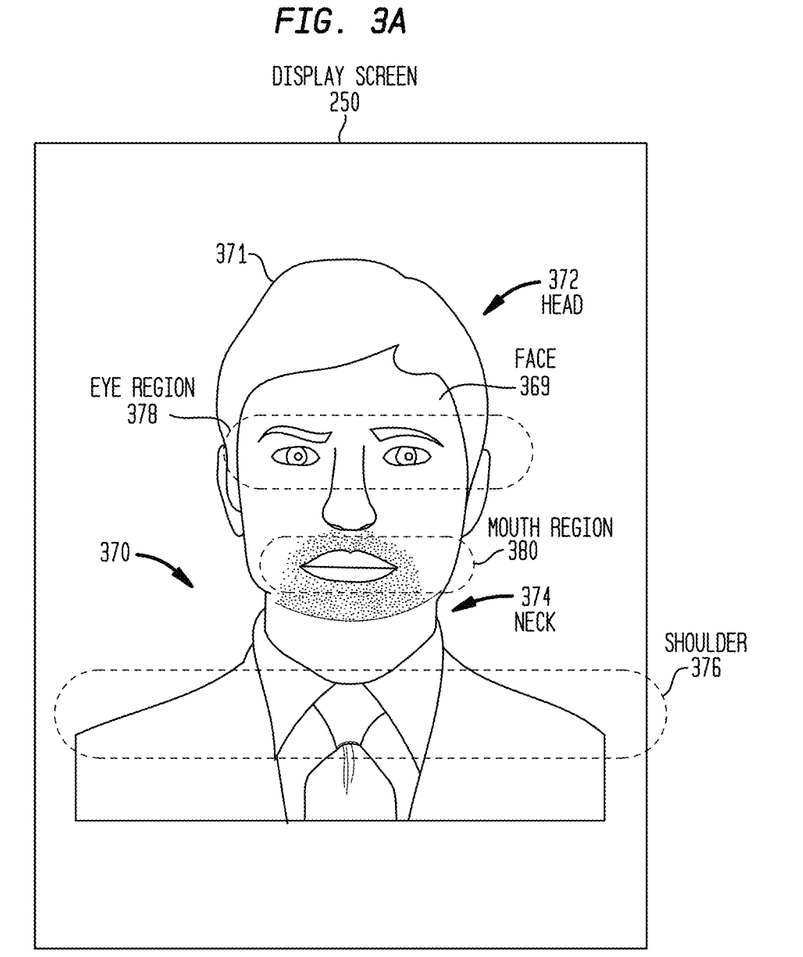
FIGS. 3A and 3B are schematic diagrams illustrating a graphical representation generated by an external device in accordance with embodiments of the present invention.

FIG. 3A is a schematic diagram of a static version of a graphical representation 370 displayed at the display screen 250 in accordance with one example implementation. As shown, the graphical representation 370 is a two-dimensional avatar 371 that includes a visual representation of a person's head 372, neck 374, and shoulder features 376. The head region 372 includes facial features 369, including an eye region 378 and a mouth region 380. The head feature 372 also includes other anatomical features, including the nose, ears, etc.

As noted, the illustration of FIG. 3A is a static version of the graphical representation 370. In accordance with embodiments presented herein, the graphical representation 370 would be animated based on the analysis of the speech signal received at the mobile phone 103. That is, the mobile phone 103 is configured to animate the graphical representation 370 to display, for example, lip movement corresponding to the speech signal, detected emotion, detected intonation, etc. (i.e., display animated visual cues generated based on the speech signals received at the mobile phone).

More specifically, using the results of the speech to lip movement synthesis, the mobile phone 103 may be configured to animate the mouth region 380 such that the lips, tongue, jaw, etc. match the content of the received speech signal (i.e., the mouth of avatar 371 is animated so as to "speak" the content of the speech signals). Additionally, using the results of the emotion and/or intonation analysis, the mobile phone 103 may be configured to, for example, animate the shoulder 376, the neck 374, and/or portions of the head 372 features, including the eye region 378 and the mouth region 380.

Figure 3B:
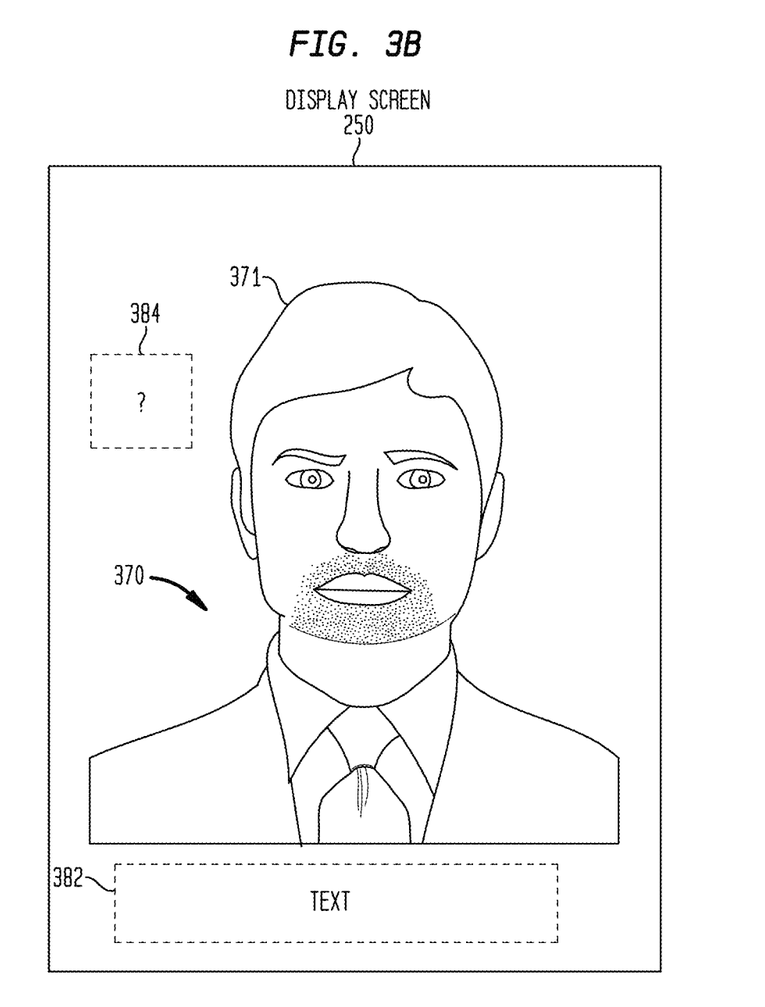

FIG. 3B illustrates the graphical representation 370 without identification of the various features and regions shown in FIG. 3A. FIG. 3B also illustrates additional features of the graphical representation 370 that were omitted from FIG. 3A for ease of illustration. For example, FIG. 3B illustrates a text region 382 that may be used to display a textual representation of the received speech signals. That is, the mobile phone 103 may be configured to convert the received speech signals into text and display that text within the region 382. FIG. 3B also illustrates a sign region 384 that may be used to provide additional information to the recipient. In one illustrative example, the sign region 384 is used to display a question mark when the mobile phone 103 determines (i.e., using emotion/intonation analysis) that the speaker of the received speech signals has asked a question.

In another embodiment, the mobile phone 103 may be configured to display a representation of a human hand or another avatar that presents sign language (i.e., manual communication). As an extension, the avatar 371 may further include hands, arms, and/or a torso to display sign language that corresponds to the received speech signals.

Is to be appreciated that the use of a question mark or sign language within sign region 384 are merely illustrative. Other signs/information may be displayed within the sign region 384 in accordance with other embodiments of the present invention.

In operation, the mobile phone 103 and/or the cochlear implant 101 is configured to correlate the animation of the visual representation 370 with the delivery of stimulation signals associated with the received speech signals. For example, animation of the mouth sub-region 380 to visualize the word "Hello" should be displayed on the display screen 250 at substantially the same time as which the cochlear implant 101 delivers stimulation signals corresponding to the word "Hello." As such, the recipient will perceive the word "Hello" through the cochlear implant 101 and at the same time visualize the avatar 371 speaking the word "Hello." Similar correlation may be utilized for the display of emotion/intonation, text, and other information.

Correlation of the animation of the graphical representation 370 with the delivery of stimulation signals by cochlear implant 101 may be performed in several manners. In one illustrative arrangement, a predetermined time delay is utilized by the mobile phone 103. More specifically, the mobile phone 103 is programmed with information indicating that the cochlear implant 101 requires a specific amount of time to process received speech signals and deliver stimulation signals to the recipient using those received speech signals. As such, the mobile phone 103 may wait the specified amount of time after transmission of the speech signals to the cochlear implant 101 before animating the visual representation in accordance with the received speech signals. In certain embodiments the period of time may be dynamically adjusted by the mobile phone and/or the cochlear implant based on a number of different factors (e.g., to account for additional processing in noisy environments).

In another illustrative arrangement, the animation of the graphical representation 370 is correlated with the delivery of stimulation signals by cochlear implant 101 using a feedback loop between the cochlear implant 101 and the mobile phone 103. In particular, the cochlear implant 101 could send a feedback signal to the mobile phone 103 indicating that a group of speech signals are being, or are about to be, delivered to the recipient. This feedback signal could trigger the mobile phone 103 to animate the graphical representation 370.

Figure 4:
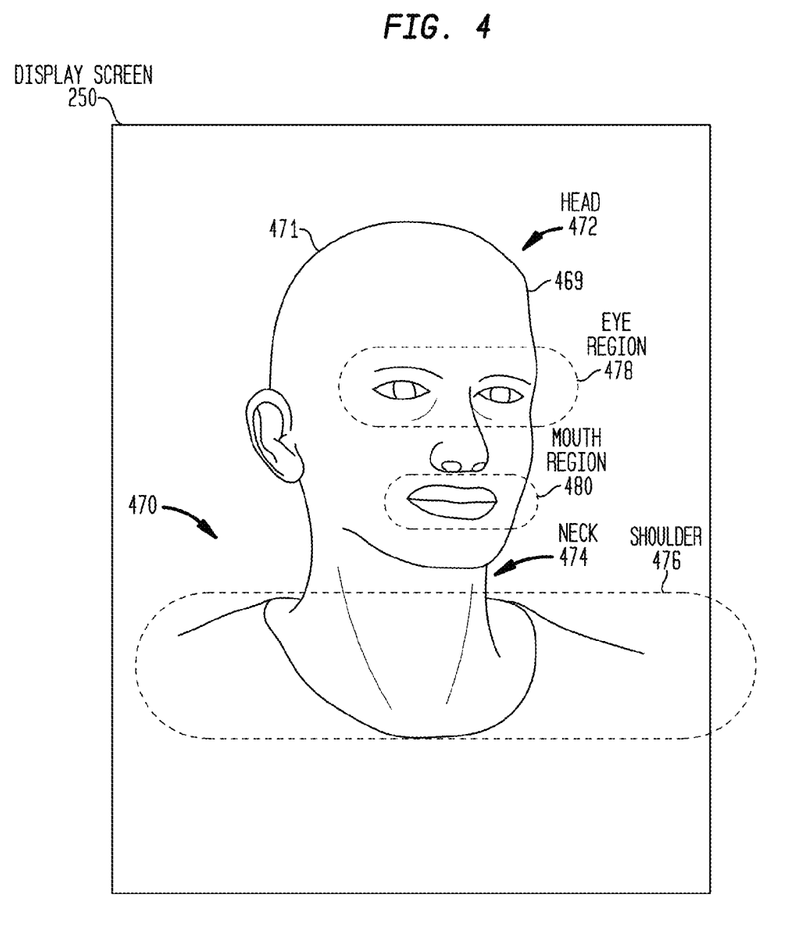
FIG. 4 is a schematic diagram illustrating another graphical representation generated by an external device in accordance with embodiments of the present invention.

As noted, FIGS. 3A and 3B illustrate an example two-dimensional graphical representation 370. It is to be appreciated that other graphical representations may be used in alternative embodiments of the present invention. For example, FIG. 4 is a schematic diagram of a static version of a three-dimensional graphical representation 470 that can be displayed at display screen 250. As shown, the graphical representation 470 comprises a three-dimensional avatar 471 that includes a visual representation of a person's head 472, neck 474, and shoulder 476 features. The head feature 472 includes an eye region 478 and a mouth region 480. The head feature 472 also illustrates other anatomical features of the face 469 and/or head, including the nose, ears, etc. In contrast to the embodiments of FIGS. 3A and 3B, the regions shown in FIG. 4 are each three-dimensional. The graphical representation 470 may also include regions for display of text or other information as described above with reference to FIG. 3B.

As noted, the illustration of FIG. 4 is a static version of the graphical representation 470. Similar to the embodiments of FIGS. 3A and 3B, the graphical representation 470 would be animated based on the analysis of the speech signal received at the mobile phone 103. The animation is also correlated with the delivery of stimulation signals by cochlear implant 101.

FIGS. 3A-4 illustrate two example avatars that may be used in embodiments of the present invention. In certain embodiments, the techniques presented herein enable the recipient or other user to customize the displayed avatar and/or program different avatars for different callers. In one specific implementation, the techniques presented herein enable the recipient or other user to load a picture or image of a caller. The techniques presented herein may be configured to display a digitized version of the caller's picture and "animate" that picture to display visual cues to the recipient. In other words, while talking to a specific caller, a digitized picture of that caller could appear on the display screen and the mobile phone 103 could animate that picture. These embodiments could enhance the user experience by enabling the recipient to also "visualize" the caller, without the need for the initiation of a video call which may require an Internet connection, additional bandwidth, or network speeds that are not also available at locations where mobile phones are utilized.

In certain embodiments of the present invention, the mobile phone 103 and/or the cochlear implant 101 is configured to detect when the mobile phone is coupled (e.g., wired or wirelessly) with the cochlear implant 101 (e.g., through execution of a pairing protocol). The mobile phone 103 may automatically display the graphical representation upon receipt of speech signals only when the mobile phone is paired with the cochlear implant 101. In further examples, the received speech signals are part of a voice call received at the mobile phone 103 (that has been previously paired with the cochlear implant 101) and the mobile phone automatically initiates display of the graphical representation when the voice call is answered at the mobile phone.

In a further example, one or more of the mobile phone 103 and/or the cochlear implant 101 may be configured to detect the presence of the other part of the auditory prosthesis system and initiate a pairing process between the mobile phone 103 and the cochlear implant 101. When a voice coil is detected, and once both these features are detected, the mobile phone 103 may automatically display the graphical representation.

In a further aspect, the embodiments presented herein enable the mobile phone 103 and/or the cochlear implant 101 to detect when a speaker is speaking in a tonal language (e.g., Chinese or Japanese). In certain embodiments, the display of the graphical may be initiated only after detection of speech associated with a tonal language.

Figure 5:
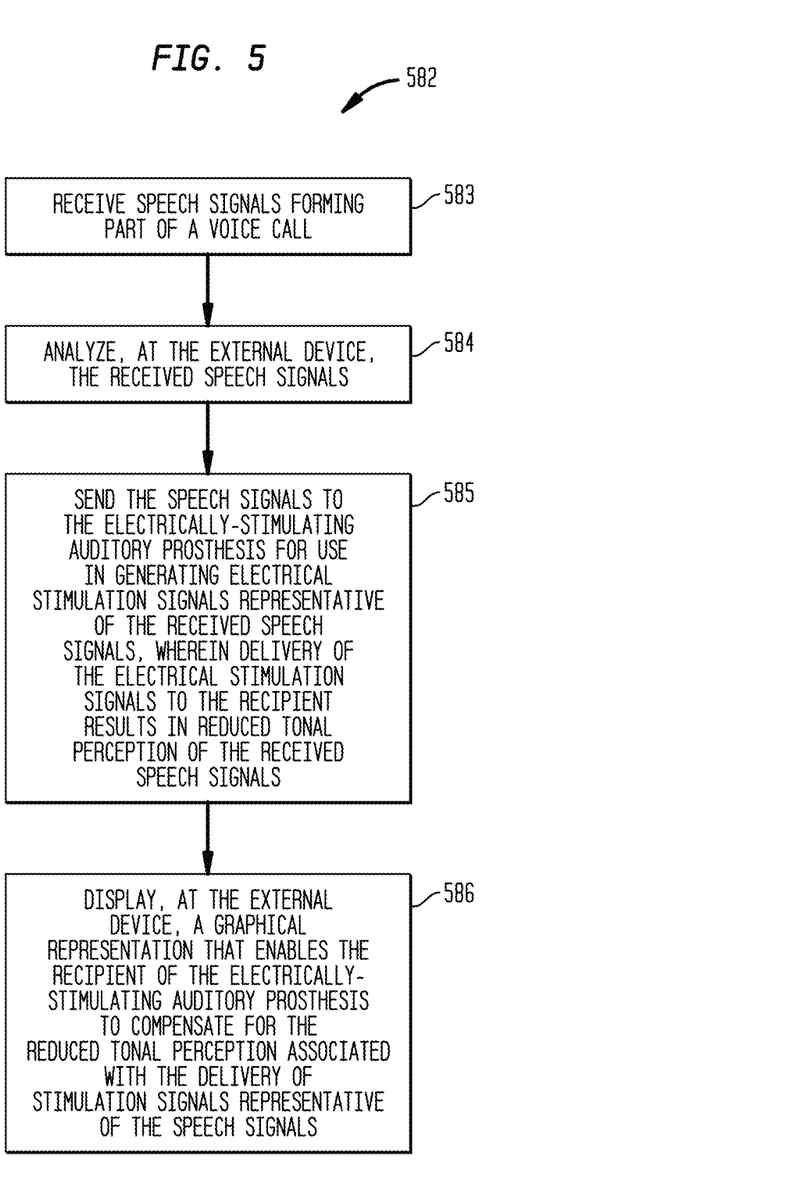
FIG. 5 is a flowchart of a method in accordance with embodiments of the present invention.

FIG. 5 is a flowchart of a method 582 in accordance with embodiments presented herein. For ease of illustration, the method 582 is described with reference to auditory prosthesis system 100, including cochlear implant 101 and mobile phone 103. Method 582 begins at 583 where the mobile phone 103 receives speech signals. The speech signals may be received, for example, over a telecommunications network as part of a voice call. At 584, the mobile phone 103 analyzes the speech signals. As noted above, the speech signal analysis may include speech to lip movement synthesis, emotion/intonation detection, etc.

At 585, the mobile phone 103 sends the speech signals to cochlear implant 101 using one of the above or other techniques. At 586, the mobile phone 103 displays a graphical representation that enables the recipient of cochlear implant 101 to compensate for reduced tonal perception associated with delivery of stimulation signals representative of the speech signals. In particular, the mobile phone 103 displays animated visual cues generated based on the received speech signals.

In certain embodiments, the graphical representation includes an avatar (e.g., humanoid avatar) that includes at least face, neck, and shoulder features/regions. In such embodiments, the animated visual cues may comprise movement/animation of one or more the features of the avatar, where the animation is based on the received speech signals. For example, the mobile phone 103 may be configured to animate features of the avatar to convey emotion and/or intonation detected from the speech signals. Additionally, the mobile phone 103 may be configured to animate a mouth region of the avatar to emulate vocal articular movements of a speaker of the received speech signals. As noted, at least one of the cochlear implant 101 and the mobile phone 103 is configured to synchronize the movement of the features of the avatar with delivery of the stimulation signals representative of the received speech signals to the recipient.

Figure 6:
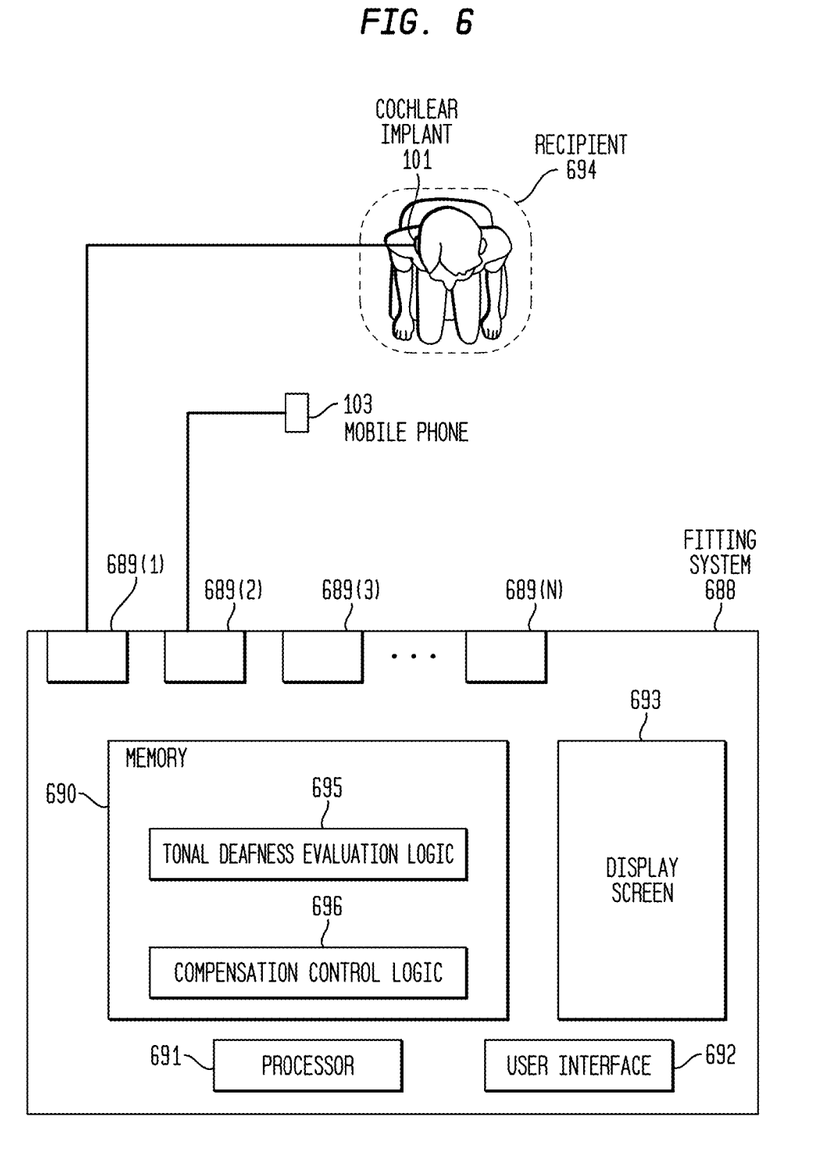
FIG. 6 is a block diagram of a fitting system in accordance with embodiments of the present invention.

Certain embodiments of the present invention are directed to a fitting system and fitting method that can be used to determine the degree of tonal deafness of a recipient of a cochlear implant and, accordingly, set the operation parameters of an auditory prosthesis system that is configured to perform the tonal deafness compensation techniques described herein. FIG. 6 illustrates an example fitting system 688 configured for use in determining the degree of tonal deafness of a recipient.

Fitting system 688 is, in general, a computing device that comprises a plurality of interfaces/ports 689(1)-689(N), a memory 690, a processor 691, a user interface 692, and a display screen 693. The interfaces 689(1)-689(N) may comprise, for example, any combination of network ports (e.g., Ethernet ports), wireless network interfaces, Universal Serial Bus (USB) ports, Institute of Electrical and Electronics Engineers (IEEE) 1394 interfaces, PS/2 ports, etc. In the example of FIG. 6, interface 689(1) is connected to cochlear implant 101 (FIG. 1) implanted in a recipient 694. Interface 689(1) may be directly connected to the cochlear implant 101 or connected to a device (e.g., remote control device, behind-the-ear processor, etc.) that is communication with the cochlear implant 101. In certain embodiments, interface 689(2) may be connected to an external device, such as mobile phone 103, that forms part of auditory prosthesis system 100. Interfaces 689(1) and 689(2) may be configured to transmit/receive signals via a wired or wireless connection (e.g., telemetry, Bluetooth, etc.).

The memory 690 includes tonal deafness evaluation logic 695 and compensation control logic 696. The tonal deafness evaluation logic 695 may be executed to determine the degree (severity) of the recipient's tonal deafness. For example, tests may be performed to assess phoneme detection, discrimination and identification task. The results of the tests may be used to classify the recipient's tonal deafness.

The compensation control logic 696 may be used to set the operational parameters of the mobile phone 103 when executing the tonal deafness compensation techniques. The fitting system 688 is configured to take into account the recipient's degree of tonal deafness when setting the operational parameters of the mobile phone 103. For example, the fitting system 688 (through execution of tonal deafness evaluation logic 695 by processor 691) may determine that the recipient 694 suffers from extreme tonal deafness (i.e., the recipient has significant difficulty in understanding speech signals in the absence of visual cues). In such an example, the fitting system 688 (through execution of compensation control logic 696) may configure the animated visual cue display logic 264 (FIG. 2) to display an animated avatar (e.g., avatar 371 of FIG. 3), text of the speech signals (e.g., within text region 382 of FIG. 3), and additional information (e.g., in signing region 384 of FIG. 3).

In another example, the fitting system 688 may determine that the recipient 694 suffers from relatively less severe tonal deafness (i.e., the recipient has some difficulty in understanding speech signals in the absence of visual cues). In such an example, the fitting system 688 may configure the animated visual cue display logic 264 (FIG. 2) to display only an animated avatar (e.g., avatar 371 of FIG. 3), without text or any other additional information.

The degree of tonal deafness of the recipient and/or the display preferences could be stored in the sound processor of the cochlear implant 101 (e.g., as part of a hearing profile) or in the mobile phone 103. In one example, the application at the mobile phone 103 could request the preference/information from the cochlear implant 103 (e.g., during a pairing process). The setting/preference (e.g., lip movement on/off, body movement on/off, text showing emotion on/off, etc.) can be made automatic or may be activated by the audiologist, clinician, or other caregiver. The cochlear implant 101 and/or the sound processor 103 could also store the language preference for speech to text translation, the avatar type, etc.

Memory 690 may comprise any one or more of read only memory (ROM), random access memory (RAM), magnetic disk storage media devices, optical storage media devices, flash memory devices, electrical, optical, or other physical/tangible memory storage devices. The processor 691 is, for example, a microprocessor or microcontroller that executes instructions for the tonal deafness evaluation logic 695 and the compensation control logic 696. Thus, in general, the memory 690 may comprise one or more tangible (non-transitory) computer readable storage media (e.g., a memory device) encoded with software comprising computer executable instructions and when the software is executed (by the processor 691) it is operable to perform the fitting operations described herein in connection with the tonal deafness evaluation logic 695 and the compensation control logic 696.

Figure 7:
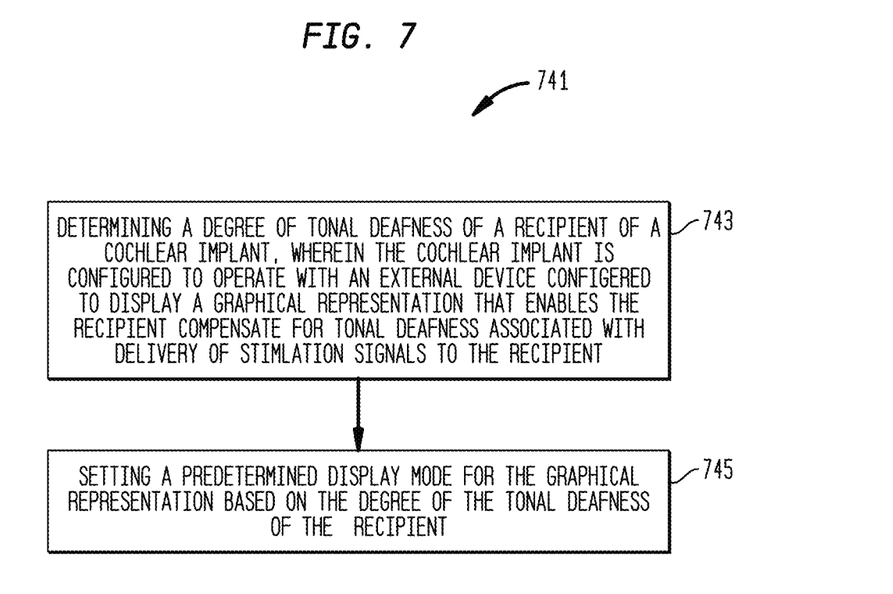
FIG. 7 is a flowchart of another method in accordance with embodiments of the present invention.

FIG. 7 is flowchart of a method 741 in accordance with embodiments presented herein. Method 741 may be at least partially performed at fitting system 688. For ease of illustration, the method 741 of FIG. 7 is described with reference to the fitting system 688 of FIG. 6.

Method 741 begins at 743 where the fitting system 688 determines a degree of tonal deafness of recipient 694 of cochlear implant 101. The cochlear 101 is configured to operate with a mobile phone 103 that is configured to display a graphical representation that includes animated visual cues associated with received speech signals. At 745, the fitting system 688 sets a predetermined display mode for the graphical representation based on the degree of the tonal deafness of the recipient.

In certain embodiments, a display mode is set in which the mobile phone 103 displays a human avatar that includes at least face, neck, and shoulder features/regions such that the mobile phone 103 can animate the features of the avatar based on received speech signals. The animation of the avatar may be synchronized with delivery to the recipient of stimulation signals representative of the received speech signals.

Embodiments have been primarily described with reference to an exemplary cochlear implant. However, as noted above, the techniques presented herein may be used with other implantable auditory prosthesis, including middle ear auditory prostheses, direct acoustic stimulators, etc. In contrast to cochlear implants that deliver electrical stimulation signals to the recipients, middle ear auditory prostheses, direct acoustic stimulators or the like deliver mechanical stimulating signals to the recipient. Certain such devices, such as certain direct acoustic stimulators, may target relatively high mixed hearing losses and may experience tonal deafness. As such, the techniques presented herein may also benefit recipients of these prostheses.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An auditory prosthesis system, comprising:
an implantable auditory prostheses configured to deliver stimulation signals to a recipient; and
an external device comprising:
an interface configured to communicate with the implantable auditory prostheses;
a display screen, and
at least one processor configured to:
provide received speech signals to the implantable auditory prostheses for use in delivering stimulation signals representative of the received speech signals to the recipient,
display, at the display screen, a graphical representation comprising a humanoid avatar that includes at least head, neck, and shoulder features, wherein the humanoid avatar is configured to enable the recipient to compensate for reduced tonal perception associated with delivery to the recipient of the stimulation signals representative of the received speech signals,
analyze the received speech signals to detect an emotion of a speaker of the received speech signals, and
animate one or more features of the avatar based on the received speech signals to convey the emotion to the recipient.

2. The auditory prosthesis system of claim 1, wherein at least one of the implantable auditory prostheses and the external device is configured to synchronize animation of the one or more features of the avatar with delivery by the implantable auditory prostheses of the stimulation signals representative of the received speech signals to the recipient.

3. The auditory prosthesis system of claim 1, wherein the avatar includes a mouth region and wherein the processor is configured to generate movement of the mouth region of the avatar that emulates vocal articulator movements of a speaker of the received speech signals.

4. The auditory prosthesis system of claim 3, wherein the received speech signals are part of a voice call received at the external device, and wherein the processor is configured to automatically initiate display of the graphical representation when the voice call is answered at the external device.

5. The auditory prosthesis system of claim 1, wherein the processor is configured to detect when the external device is coupled with the implantable auditory prostheses, and wherein the processor is configured to automatically display the graphical representation upon receipt of the received speech signals only when the external device is coupled with the implantable auditory prostheses.

6. The auditory prosthesis system of claim 1, wherein the external device is a mobile phone.

7. The auditory prosthesis system of claim 1, wherein the external device is a tablet computer.

8. The auditory prosthesis system of claim 1, wherein the implantable auditory prostheses is a cochlear implant.

9. The auditory prosthesis system of claim 8, wherein the cochlear implant is a totally implantable cochlear implant.

10. A method performed at a system that includes an implantable auditory prosthesis and an external device, comprising:
receiving speech signals forming part of a voice call;
analyzing, at the external device, the received speech signals;
sending the speech signals to the implantable auditory prosthesis for use in generating stimulation signals representative of the received speech signals, wherein delivery of the stimulation signals to the recipient results in reduced tonal perception of the received speech signals;
displaying, at the external device, a graphical representation comprising a humanoid avatar that includes at least a head with a mouth region, wherein the humanoid avatar enables the recipient of the implantable auditory prosthesis to compensate for the reduced tonal perception associated with delivery of stimulation signals representative of the speech signals;
performing speech to lip movement synthesis of the received speech signals; and
animating the mouth region of the avatar based on the received speech signals so as to emulate vocal articulator movements of a speaker of the received speech signals.

11. The method of claim 10, further comprising:
synchronizing the animation of one or more features of the avatar with delivery by the implantable auditory prosthesis of the stimulation signals representative of the received speech signals to the recipient.

12. The method of claim 10, further comprising:
performing emotion detection of the received speech signals; and
animating one or more of the features of the avatar to convey the detected emotion to the recipient.

13. The method of claim 10, further comprising:
detecting when the external device is coupled with the implantable auditory prosthesis; and
automatically displaying the graphical representation upon receipt of the received speech signals only when the external device is coupled with the implantable auditory prosthesis.

14. The method of claim 10, wherein the received speech signals are part of a voice call received at the external device, and further comprising:
automatically initiating display of the graphical representation when the voice call is answered at the external device.

15. A method, comprising:
determining a degree of tonal deafness of a recipient of an implantable auditory prosthesis, wherein the implantable auditory prosthesis is configured to operate with an external device configured to display a graphical representation that enables the recipient to compensate for tonal deafness associated with delivery of stimulation signals to the recipient; and
based on the degree of the tonal deafness of the recipient, setting a predetermined display mode for the graphical representation in which the external device displays a humanoid avatar that includes at least a head that includes a mouth region; and
animating the mouth region of the avatar based on the received speech signals so as to emulate vocal articulator movements of a speaker of the received speech signals.

16. The method of claim 15, wherein displaying a graphical representation in accordance with the predetermined display mode comprises:
displaying animated visual cues with the humanoid avatar, where the visual cues are generated based on the received speech signals.

17. The method of claim 15, further comprising:
synchronizing the animation of one or more features of the avatar with delivery to the recipient of stimulation signals representative of the received speech signals.

18. The method of claim 15, further comprising:
analyzing the received speech signals to detect an emotion of a speaker of the received speech signals; and
animating one or more of features of the avatar to convey the emotion to the recipient.

19. The method of claim 15, further comprising:
setting a display mode in which text is displayed as part of the graphical representation; and
generating, based on received speech signals, text for display as the graphical representation.

20. The method of claim 15, further comprising:
storing a degree of tonal deafness as a hearing profile in at least one of the implantable auditory prosthesis or the external device.

* * * * *